(12) United States Patent
Bracci

(10) Patent No.: US 8,491,555 B2
(45) Date of Patent: Jul. 23, 2013

(54) ABSORBENCY PAD FOR USE IN NEONATAL CARE AND RELATED METHOD OF USE

(76) Inventor: Jennifer J. Bracci, Palmetto Bay, FL (US)

( * ) Notice: Subject to any disclaimer, the term of this patent is extended or adjusted under 35 U.S.C. 154(b) by 359 days.

(21) Appl. No.: 12/898,835

(22) Filed: Oct. 6, 2010

(65) Prior Publication Data
US 2011/0082433 A1     Apr. 7, 2011

Related U.S. Application Data

(60) Provisional application No. 61/248,982, filed on Oct. 6, 2009.

(51) Int. Cl.
*A61F 13/15*    (2006.01)
(52) U.S. Cl.
USPC ............. 604/385.11; 604/385.14; 604/385.28
(58) Field of Classification Search
USPC ............................ 604/385.11, 385.14, 385.28
See application file for complete search history.

(56) References Cited

U.S. PATENT DOCUMENTS

| | | | | |
|---|---|---|---|---|
| 5,662,636 A | * | 9/1997 | Benjamin et al. | 604/385.28 |
| 2004/0039363 A1 | * | 2/2004 | Sugiyama et al. | 604/385.101 |
| 2007/0003603 A1 | * | 1/2007 | Karandikar et al. | 424/443 |
| 2007/0056096 A1 | * | 3/2007 | Assink | 5/81.1 HS |

* cited by examiner

*Primary Examiner* — Jacqueline F. Stephens
(74) *Attorney, Agent, or Firm* — Allen, Dyer, Doppelt, Milbrath & Gilchrist, P.A.

(57) ABSTRACT

The invention is directed to a planar pad manufactured from three bonded layers each having different properties and materials. This includes a contact layer having a first and corresponding second portion. The second portion overlaps the first portion sufficient to create a first overlay. Such contact layer may be made of fibers which include silver nano-particulates. The contact layer may also include a coating made of TEFLON or similar material. The second layer is an absorbency layer positioned immediately below the contact layer. The absorbency layer being made of natural woven bamboo fiber. In addition, the absorbency layer may be two-part construction having a first absorbent portion and a corresponding second absorbent portion which abuts the first absorbent portion, wherein both absorbent portions have fused sides to reduce fraying. The third layer is a waterproof barrier layer which is posited directly below the absorbency layer, preferably constructed of TYVEK.

5 Claims, 3 Drawing Sheets

ABSORBENCY PAD FOR USE IN NEONATAL CARE AND RELATED METHOD OF USE

CROSS-REFERENCE TO RELATED APPLICATION

This application seeks priority to U.S. Provisional Patent Application Ser. No. 61/248,982 filed on Oct. 6, 2009 entitled "Perforated Absorbency Pad for Use in Neonatal Care," the contents of which are incorporated by reference herein.

FIELD OF THE INVENTION

This invention is directed toward an absorbency pad for use with low birth weight or unstable infants incubated in a neonatal intensive care unit that reduces the amount of contact with the infant.

BACKGROUND OF THE INVENTION

Premature birth, also commonly known as preterm birth, occurs when the infant is born after less than 37 weeks of gestation. Statistically, premature infants are at a greater risk of short and long-term complications, including impediments in growth and mental development. Long term health effects resulting from preterm birth can include cerebral palsy, blindness, lung disease, and learning disabilities. While the underlying cause of preterm birth is generally unknown, many factors appear to be associated with premature birth—making reduction of this health risk challenging.

In most developed countries and in Europe, the preterm birth rate is generally between 5 to 9 percent. However, in the United States, the rate has risen to an alarming 12 to 13 percent over the last several decades. In fact from 1990 to 2005, premature births in this country have risen over 20 percent. This translates to roughly 500,000 preterm births each year.

There are several classifications of preterm birth, based largely upon the gestational age and birth weight. A low birth weight infant (LBW) refers to any infant weighing less than 5 pounds, 8 ounces. A very low birth weight infant ("VLBW") includes an infant born less than 3 pounds, 5 ounces. Finally, an extremely low birth weight infant ("ELBW") is an infant who weighs less than 2 pounds, 2 ounces. Each year, approximately 40,000 ELBW infants are born in the United States.

Most hospitals in developed countries maintain neonatal intensive care units ("NICUs") capable of treating preterm infants, as well as low birth weight infants (including VLBW and ELBW infants) or any infant requiring hospital intervention. Highly trained and specialized nurses who are capable of treating neonatal infants staff these NICUs. Most NICUs keep neonatal infants in specialized incubators that create a confined and isolated environment to provide regulated temperature and proper life support and respiratory systems.

When treating neonatal infants, especially VLBW and ELBW infants, most NICUs attempt to reduce or even eliminate physical contact as much as possible for the first 72 hours after birth (once these infants are placed into an incubator (or onto a radiant warmer) and connected to life support, respiratory systems and monitors). This is because these neonatal infants have extremely fragile skin, high sensitivity to touch, and are at a larger risk of intraventricular hemorrhaging (a rupturing of the capillaries in the brain, which can be caused in part in handling low birth weight infants).

Due to these risks, doctors and nurses try to adhere to a minimal stimulation protocol by clustering care, for example, to allow babies longer periods of rest. Currently, however, there is no simple or safe way to change neonatal bed linens. Instead, it is simply common practice to place an absorbent cotton blanket in the incubator (or on the radiant warmer) prior to treating the neonatal infant. Once a blanket becomes soiled with blood, urine, feces or materials used to treat the neonatal infant (i.e., betadine or saline), they are removed from the incubator or radiant warmer. This typically occurs through briefly lifting the neonatal infant, removing the soiled blanket and positioning a new and clean blanket (requiring multiple staff assisting in this process).

There are multiple drawbacks with this current system commonly used in NICUs. First, the brief relocation of the neonatal infant to remove the soiled blankets can cause trauma, bruising or even possible intraventricular hemorrhaging. Second, repositioning the neonate to remove the soiled blanket risks extubation of endotracheal tubes required for ventilation, which can cause damage, injury or even death to the neonate—or at the very least severe discomfort. Finally, even with removal of the top layered blanket, there is a risk that some secretion of fluid could have seeped onto the underlying incubator (or radiant warmer). Upon removal of the top cotton blanket, the neonatal infant is still exposed to this fluid risking infection.

Accordingly, there is a need in the art of treating neonatal infants—especially those with VLBW and ELBW—or any unstable newborn within an incubator or radiant warmer to reduce the amount of physical contact with NICU nurses. Moreover, there is a need in the art of manufacturing bed barriers to allow removal of soiled bed blankets without disrupting or moving the neonatal infant to reduce the risk of trauma and/or injury.

SUMMARY OF THE INVENTION

The present invention solves the current problems faced in the art of linen changes for neonatal infants in NICU incubators or radiant warmers. In addition, the present invention includes a method for removing soiled blankets with minimal impact on the neonatal infant, thereby reducing the risk of trauma or injury.

In one embodiment, the invention is directed to a pad that is essentially planar having an upper side, a lower side, a first side and a corresponding second side. Preferably, the pad is manufactured from three bonded layers each having different properties and constructed from different materials. This includes a contact layer having a first portion and a corresponding second portion. The second portion overlaps the first portion sufficient to create a first overlay. Such contact layer may be made of fibers which include silver nano-particulates. The contact layer may also include a coating made of Teflon™ or similar non-stick material.

The second layer is an absorbency layer positioned immediately below and juxtaposed the contact layer. The absorbency layer may be made of natural woven fiber material. Preferably, the absorbency layer is made of woven bamboo fabric. However, a non-woven bamboo layer is also contemplated. In addition, the absorbency layer may be two-part construction having a first absorbent portion and a corresponding second absorbent portion which abuts the first absorbent portion, wherein both absorbent portions have fused sides to reduce fraying.

The third layer is a waterproof barrier layer which is posited directly below the absorbency layer. Such barrier layer may be the same length and width as the contact layer. In addition, such barrier layer may have a first barrier portion and second barrier portion sufficient to create a second overlay. Preferably, the barrier layer may be made of a flashspun high-density polyethylene material. The invention contemplates placement of two or more absorbency pads together arranged in a notepad configuration such that the upper side of each pad in glued to the other. Such notepad arrangement may include a rigid bottom having the same length and width of each absorbency pad.

The invention is also directed to a method of treating a neonate infant, in order to reduce the risk of tearing or bruising the skin while removing a soiled pad. The method first comprises the step of placing a first pad onto a bed portion of a NICU incubator and then adding a second pad onto the first pad, the second pad having the same components as the first pad. The second step is to determine whether the second pad has becomed soiled by the neonatal infant. If so, the last step is to detach the first portion of the contact layer from the second portion of the contact layer by pulling apart the second pad.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The Pad

Figure 1:
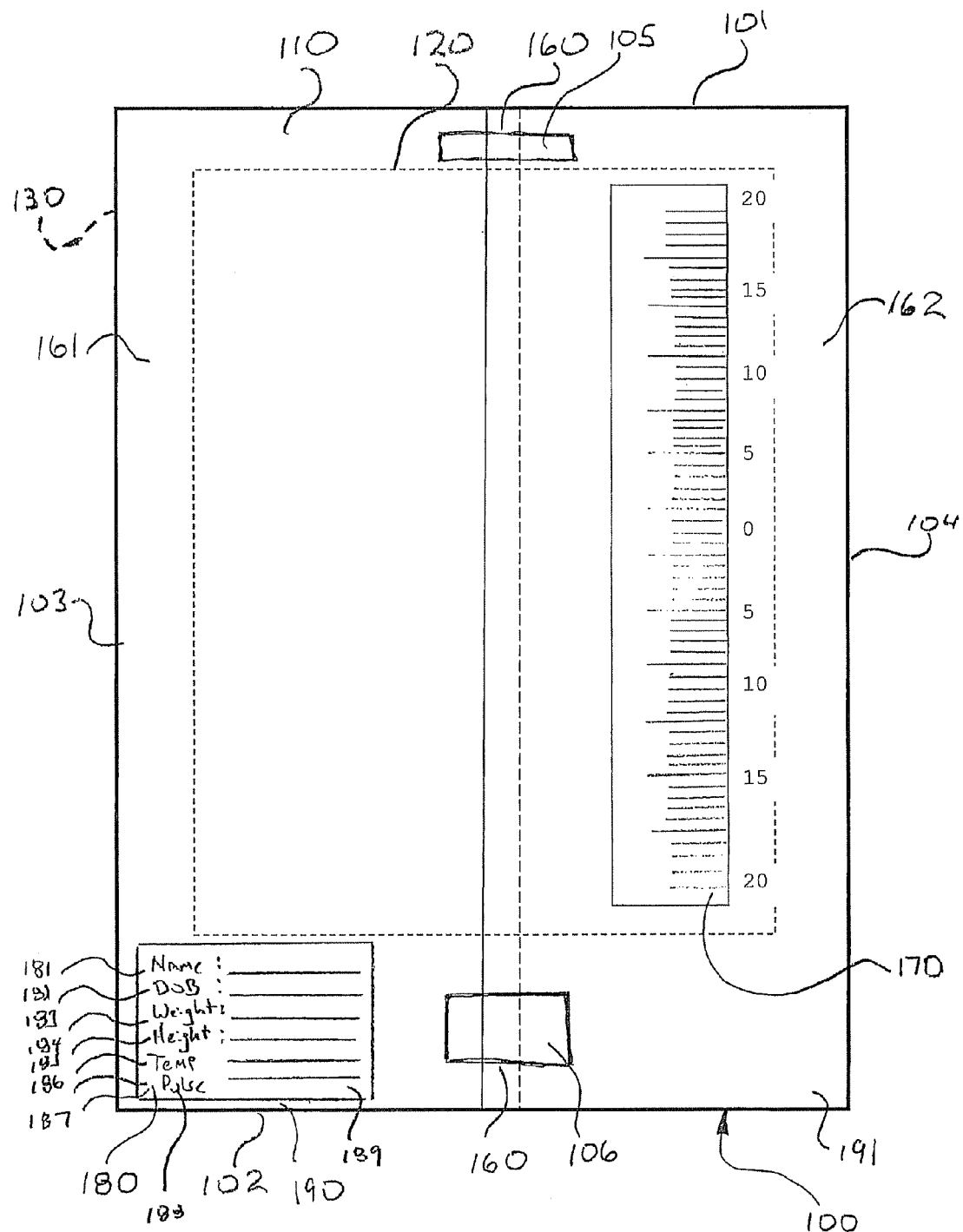
FIG. 1 is a top view of the perforated multi-layer pad that includes a ruler and recording area.
Figure 2:
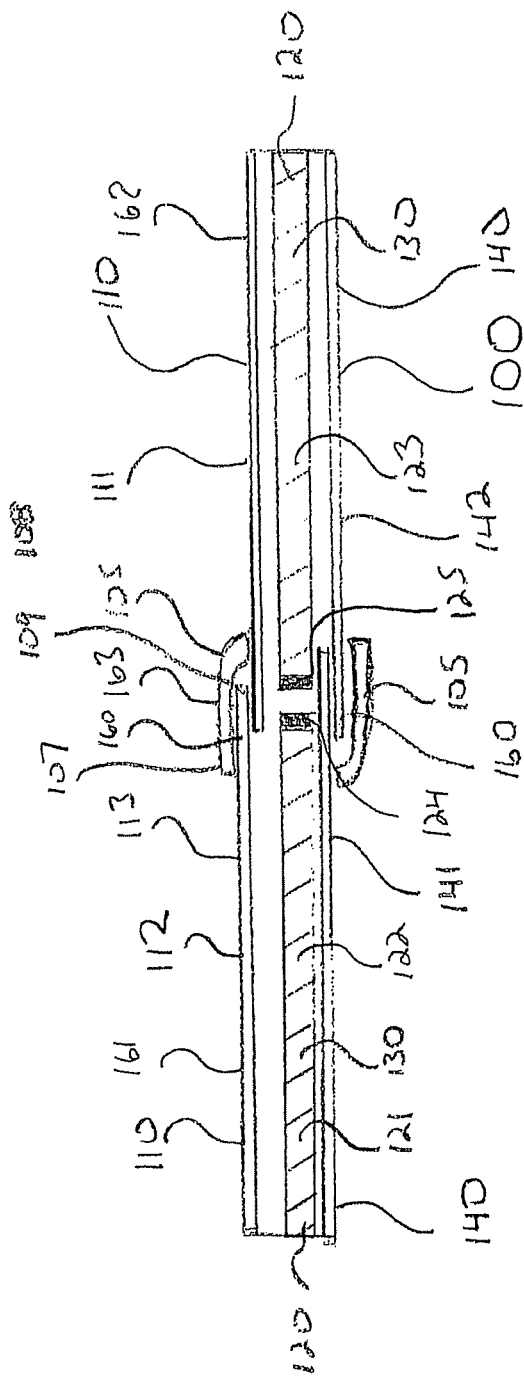
FIG. 2 is a side view of the two-part perforated pad shown in FIG. 1.

As shown in FIG. 1 and FIG. 2, the invention is directed to a pad 100 having a plurality of layers including a contact layer 110, an absorbency layer 120 and a barrier layer 140. As shown in FIG. 1, the pad 100 is essentially rectangular and includes an upper edge 101, a lower edge 102, a left side edge 103, and a right side edge 104. Moreover, the pad 100 is of a sufficient size and dimension to be placed and maintained within a NICU incubator (or radiant warmer) 200 (shown in FIG. 3).

As further illustrated in FIG. 1, located approximately in the middle of the pad 100 is a bifurcation 160 that divides the pad 100 into a first portion 161 and a second portion 162. The bifurcation 160 is preferably created through an overlap of the two portions 161 and 162 of the contact layer 110, a similar overlap with the barrier layer 140. Such overlap may be secured by a first fastener 105 positioned near the upper edge 101, as well as a second fastener 106 located near the lower edge 102 of the pad 100. In addition, such bifurcation 160 can be a perforation, instead of an overlap secured by a series of fasteners 105 and 106. Regardless, such bifurcation 160 extends from the upper edge 101 to the lower edge 102. By pulling the left side edge 103 of the pad 100 apart and away from its right side edge 104, the bifurcation 160 causes the first portion 161 to detach from the second portion 162 (through breaking fasteners 105 and 106 which are preferably above and below the neonatal infant).

Apart from a bifurcation 160, FIG. 1 further illustrates how the pad 100 can include a depiction of a ruler 170 or similar measuring device located on the absorbency layer 120. Such ruler 170 preferably includes a wetness indicator. Once a neonatal infant 300 is placed onto the pad 100, her height can be measured through use of the ruler 170 without moving or disturbing the neonatal infant 300—thus reducing risk of trauma and/or injury. It is preferably that the ruler 170 be positioned and located at or proximate to the bifurcation 160 of the pad 100.

In addition, the contact layer 110 of the pad 100 can include a recording area 180. The recording area 180 allows a nurse or medical professional to denote current medical information 181 relating to a neonatal infant 300. Such medical information 181 can include (but is certainly not limited to) the patient name 182, date of birth 183, time of birth 184, weight 185, measurements (including head circumference, chest circumference, abdominal girth, length) 186, pulse (including respiratory rate and blood pressure) 187, temperature 188, and location of intravenous access 189. While the recording area 180 can be placed in any location on the absorbency layer 120, it is preferable to position it in either the bottom left 190 or bottom right side 191 of the pad 100.

The Contact Layer

As illustrated in FIG. 2, the pad 100 includes a contact layer 110. Such contact layer 110 is preferably positioned at the top surface of the pad 100 such that it is the layer which interacts with the neonatal infant. This contact layer 110 constitutes the top portion of the pad 100 which is in direct contact with the neonatal infant while being incubated. Thus, the contact layer 110 must be capable of absorbing a variety of bodily fluids such as urine, feces, blood and other discharge while the neonatal infant is being treated in the NICU. This contact layer 110 must also absorb and contain other treating fluids used during incubation in the NICU such as betadine, saline or ointment.

Preferably, the contact layer 110 is manufactured from a soft, smooth and non-stick material 111. While such layer is non-abrasive and hypoallergenic, the contact layer 110 should be designed such that is not too slick. Several materials 111 can be used for the contact layer 110 including both woven and non-woven materials—which can be either natural or synthetic fibers. Preferably, the material 111 for the top of the pad 100 is preferably a blend of polymer fibers 112 which are preferable coated with Teflon™ or a similar non-stick material. Interdisbursed throughout the polymer fibers 112 are nano-silver particulates 113. Such nano-silver particulates 113 help reduce bacterial and microbial build-up on the contact layer 110. While several commercially available nano-silver particulates 113 can be used based upon their bacteriostatic and antimicrobial properties, it is preferable to use nanosilver particulates. However, it is important to note that the addition of such nano-silver particulates 113 does not render the pad 100 non-xray compatible or similar imaging procedures.

As shown in FIG. 1, the contact layer 110 includes a bifurcation 160 such that the pad 100 can be split into two portions 161 and 162 for removal away from the neonate infant. Such bifurcation 160 may include use of an overlay 163 where the first portion 161 of the contact layer 110 overlaps the second portion 162. To ensure that the overlay 163 does not become dislodged during use of the pad 100, the contact layer 110 includes one or more fasteners 105. Each fastener 105 is designed to be easily removed without risk of tearing or damaging the contact layer 110 while such bifurcation 160 is separated when changing out the pad 100.

While the fasteners 105 can be a variety of structures sufficient to engage both portions 161 and 162, they are preferably adhesive tabs 107 and 108. As illustrated in FIG. 1, a first adhesive tab 107 serves as a first fastener 105 to engage both portions 161 and 162 of the contact layer 110. Preferably, the first adhesive tab 107 is positioned proximate the upper edge 101 of the pad 100 along the contact edge 109 formed by overlap of portions 161 and 162. Correspondingly, a second adhesive tab 108 is positioned proximate the lower edge 102 of the pad also along the contact edge 109.

Preferably, the adhesive tape 107 is essentially a flat planar sheet manufactured of a polymer material. Moreover, each flat planar sheet includes a top side and a corresponding bottom side. The top side resembles the same characteristics of the contact layer 110 of the pad 100, namely a smooth, soft and hypoallergenic material so as not to cause any irritation. In contrast, the bottom side of the planar sheet includes an adhesive material sufficient to engage both the first portion 161 and second portion 162 of the contact layer 110.

The Absorbency Layer

In addition to a contact layer 110, the pad 100 also preferably includes an absorbency layer 120. As shown and illustrated in FIG. 2, the absorbency layer 120 is positioned and located immediately below and juxtaposed to the contact layer 110. Preferably, the length and width of the absorbency layer 120 should mirror that of the contact layer 110. In addition, both the contact layer 110 and absorbency layer 120 should be bonded to one another.

The absorbency layer 120 is preferably made of natural fibers, woven together, capable of absorbing various organic fluids. Alternatively, such absorbency layer 120 can be manufactured from a high absorbency natural fill—instead of a woven natural fiber. Regardless of structure (fill or fiber, or woven or non-woven), it is preferable that the natural fiber be made out of bamboo due to its high absorbency and antimicrobial properties. However, other natural fibers such as merino wool and cotton are also contemplated.

In addition, the absorbency layer 120 can include a thermo-chemical 121 that allows detection of a fever and/or sudden change in body temperature. For example, should the neonatal infant 300 maintain a temperature above average, the thermo-chemical 121 located on the pad 100 will turn a distinct color to alert the NICU of a potential medical issue.

Finally, it is contemplated that the outer edges of the absorbency layer 120 include certain colors (for example green color) that may be calming or healing to the neonatal infant. Thus, the pad 100 can also have possible benefits of chromotherapy for holistic healing. A variety of thermo-chemicals 121, known to those of ordinary skill in the art, can be used. As an alternative, an exothermic chemical 121 can be included in the absorbency layer 120 sufficient to provide additional warmth to the neonatal infant while being treated in the NICU incubator.

Such absorbency layer 120 can also act as a treating layer 130. The treating layer 130 includes certain medicines 131 to help prevent injury to the neonatal infant 300. These medicines 131 can include, but are not limited to, antibacterial ointment 132 (such as Benzalkonium Chloride 0.1%), antibiotic ointment 133, antimicrobial ointment 134, a general moisturizing agent 135 and/or an antifungal agent 136.

Like the contact layer 110, the absorbency layer 120 is of two-part construction such that it has a first absorbency portion 122 and a corresponding second portion 123. The first absorbency portion 122 includes a first fused end 124 at its distal point, while the corresponding second absorbency portion 123 includes a second fused end 125. Unlike the contact layer 110 there is no overlap or overlay between portions 122 and 123 of the two-part constructed absorbency layer 120. Rather, both portions 122 and 123 abut one another.

To ensure that both portions 122 and 123 do not become unraveled, both fused ends 124 and 125 are sufficiently stitched or fused to reduce any risk of fraying. This also helps ensure that once the bifurcation 160 of the contact layer 120 is separated, that both portions 122 and 123 can easily disjoin in order to allow a soiled/spent pad 100 to be removed from the incubator.

The Barrier Layer

As further shown in FIGS. 1 and 2, the pad 100 also preferably includes a barrier layer 140. As shown in FIG. 2, this barrier layer 140 is located below both the contact layer 110 and absorbency layer 120. The barrier layer 140 is preferably manufactured of a synthetic material that is sufficiently water-proof or leak proof to prevent bodily fluids (urine, blood, and feces) as well as treating fluids (betadine and saline) from leaking below the pad 100. Preferably, the barrier layer 140 is made of TYVEK or similar flashspun high-density polyethylene material known to those of ordinary skill in the art.

Akin to the contact layer 110, the barrier layer 140 includes a bifurcation 160. This bifurcation 160 includes two overlapping barrier portions 141 and 142. Both overlapping barrier portions 141 mirror the overlap and dimensions as portions 161 and 162 of the contact layer 110.

Figure 3:
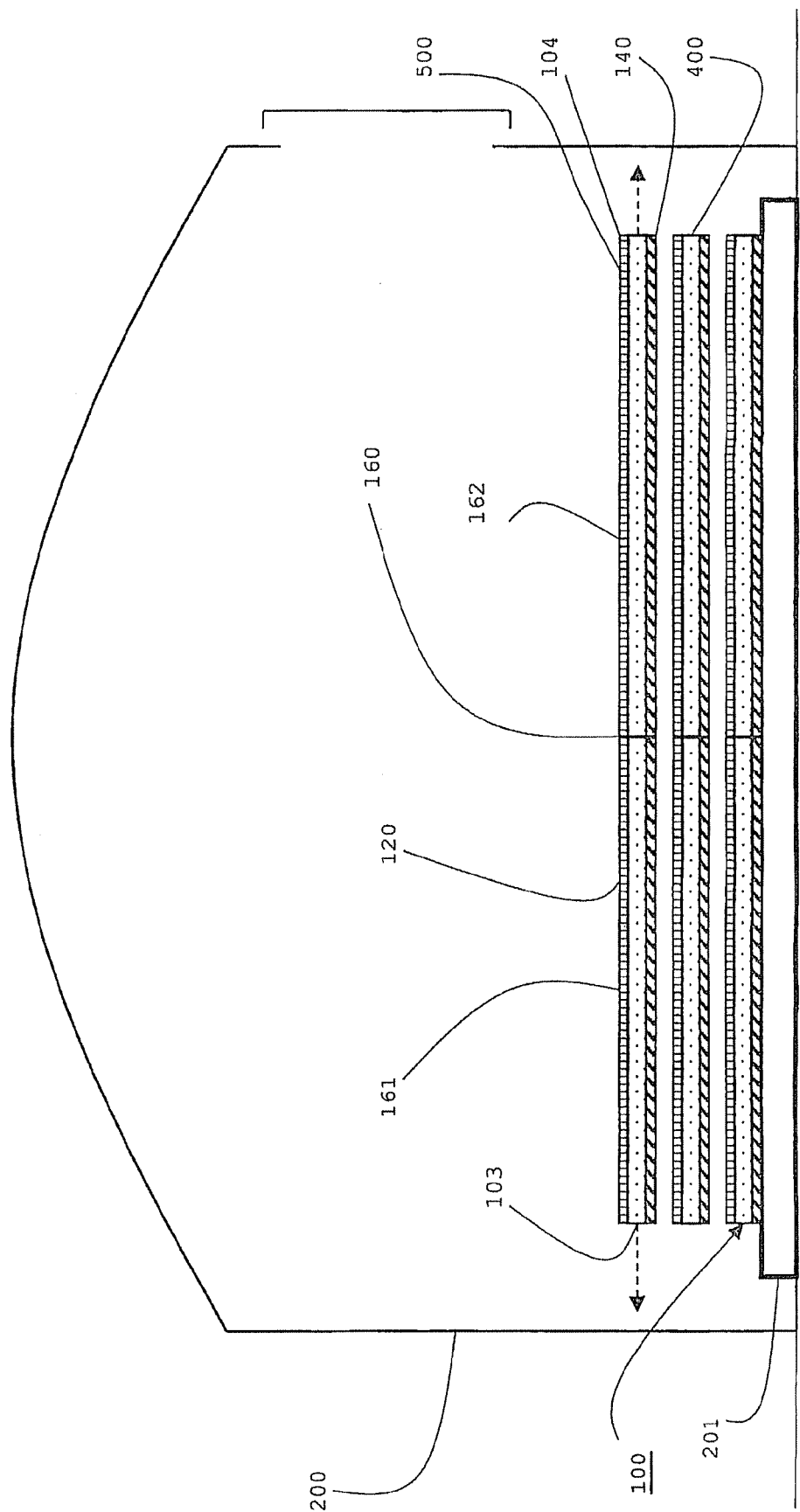
FIG. 3 is a side view of the apparatus shown in FIG. 1 and FIG. 2 positioned within a NICU incubator.

As shown in FIG. 3, the invention contemplates placement of two or more absorbency pads 100 together arranged in a notepad configuration such that the upper edge 101 of each pad 100 are glued to the other (or affixed such that they can be removed via a perforation). Such notepad arrangement can include a rigid bottom footer having the same length and width of each absorbency pad 100. Such rigid bottom footer is capable of holding between six to ten pads together as one single unit.

Method of Use

In addition to the apparatus described above, the invention is further directed toward using a pad 100 to treat a neonatal infant 300 treated in a NICU incubator (or radient warmer) 200. FIG. 3 illustrates how the pad 100 is properly used to provide this treatment. The method first begins with the step of placing a first pad 100 onto the bed portion 201 of the NICU incubator. Next, one or more additional middle pads 400 (including a top pad 500) are placed on top of the first pad 100. Upon determining that that the top pad 500 has become soiled by the neonatal infant 300 (or through treating the neonatal infant 300), the top pad 500 is detached by pulling the left side edge 103 of the top pad 500 apart and away from its right side edge 104 such that the bifurcation 160 causes the portion 161 to detach from the side portion 162 of the contact layer 110 (as well as the first barrier portion 141 and second barrier portion 142 of the barrier layer 140). An additional related step when detaching these various portions 141, 142, 161 and 162 is to break the fasteners 105 and 106 from the contact layer 110.

Great caution should be used when detaching portion 161 from portion 162 to ensure that the neonatal infant 300 is not injured (by breaking or bruising his skin). Upon detaching both portions 161 and 162 (as well as barrier portions 141 and 142), the neonatal infant 300 can rest on a clean pad 400. This method can repeat itself until there are no more additional clean pads 100, 400 or 500 or the baby is stable enough to remain on baby blankets and tolerate tradition linen changes.

In addition, the method can include measuring the length of the neonatal infant 200 through use of the ruler 170 (shown in FIG. 1). As shown in FIG. 1, such measurement can be achieved by adding the value above the zero line marker and below the zero line marker. Such zero line marker allows accurate length measurement without need to move the neonate infant. Moreover, the method can further comprise the step of recording medical information 181 regarding the neonatal infant 300 in a specific recording area 180. This medical information 181 recorded on the pad 100 can include the patient name 182, date of birth 183, time of birth 184, weight 185, length 186, pulse 187, temperature 188, and intravenous access 189. Other records possible on the pad 100 can include blood pressure, resting heart rate, and oxygen saturations.

To ensure the overall health and well being of the neonatal infant 300, the method can also include activation of an exothermic chemical 121 to warm the pad 100. In addition, the pad 100 is preferably monitored to determine if the thermochemical 121 has changed colors suggesting a potential fever.

I claim:

1. A method of treating a neonate infant, the method comprising the steps of:
    (a) placing a first pad onto a bed portion of a NICU incubator, the first pad including a contact layer having a first portion and a corresponding second portion which overlaps the first portion sufficient to create a first overlay, an absorbency layer positioned immediately below the contact layer, the absorbency layer being made of woven bamboo fibers, and a waterproof barrier layer positioned below the absorbency layer, the barrier layer having essentially the same length and width as the contact layer and having a first barrier portion and second barrier portion sufficient to create a second overlay;
    (b) adding a second pad onto the first pad, the second pad having essentially similar construction as the first pad;
    (c) determining whether the second pad has become soiled by the neonatal infant; and
    (d) detaching the first portion of the contact layer from the second portion of the contact layer by pulling apart the second pad.

2. The method of claim 1, further comprising the step of:
    breaking a fastener located at the upper edge of the contact layer, wherein the fastener engages both the first portion and second portion of the contact layer.

3. The method of claim 2, wherein the fastener is an adhesive tab having a top side and a corresponding bottom side, wherein the bottom side includes an adhesive material.

4. The method of claim 1, wherein the contact layer is made of fibers which include silver nano-particulates.

5. The method of claim 1, wherein the waterproof barrier layer is made of a flashspun high-density polyethylene material.

* * * * *